United States Patent [19]

de Coriolis et al.

[11] Patent Number: 5,083,562
[45] Date of Patent: Jan. 28, 1992

[54] METHOD AND APPARATUS FOR APPLYING ASYMMETRIC BIPHASIC TRUNCATED EXPONENTIAL COUNTERSHOCKS

[75] Inventors: Paul E. de Coriolis; John R. Batty, Jr., both of Miami, Fla.; Bruce J. Shook, North Andover, Mass.

[73] Assignee: Telectronics Pacing Systems, Inc., Englewood, Colo.

[21] Appl. No.: 574,510

[22] Filed: Aug. 28, 1990

Related U.S. Application Data

[63] Continuation of Ser. No. 397,637, Aug. 23, 1989, abandoned, which is a continuation of Ser. No. 145,515, Jan. 19, 1988, abandoned.

[51] Int. Cl.$^5$ ............................................. A61N 1/36
[52] U.S. Cl. ................................................ 128/419 D
[58] Field of Search ................................. 128/419 D

[56] References Cited

U.S. PATENT DOCUMENTS

| | | | |
|---|---|---|---|
| 3,224,447 | 12/1965 | Becker et al. | 128/421 |
| 3,614,955 | 10/1971 | Mirowski et al. | 128/419 D |
| 4,120,305 | 10/1978 | Rhoads et al. | 128/405 |
| 4,498,478 | 2/1985 | Bourgeois | 128/419 PG |
| 4,576,170 | 3/1986 | Bradley et al. | 128/419 D |
| 4,637,397 | 1/1987 | Jones et al. | 128/419 D |
| 4,800,883 | 1/1989 | Winstrom | 128/419 D |
| 4,821,723 | 4/1989 | Baker, Jr. et al. | 128/419 D |
| 4,830,006 | 5/1989 | Haluska et al. | 128/419 PG |
| 4,850,357 | 7/1989 | Bach, Jr. | 128/419 D |
| 4,953,551 | 9/1990 | Mehra et al. | 128/419 D |

FOREIGN PATENT DOCUMENTS

0281219 9/1988 European Pat. Off. .

OTHER PUBLICATIONS

W. B. Kouwenhoven, *Annals of Internal Medicine*, vol. 71, No. 3, pp. 449-458 (Sep., 1969).
Langer et al., "Considerations in the Development of the Automatic Implantable Defibrillator," *Medical Instrumentation:* vol. 10, No. 3; May-Jun. 1976; pp. 163-167.
Mirowski et al., "Termination of Malignant Ventricular Arrhythmias with an Implanted Automatic Defibrillator in Human Beings," *New Eng. Journal of Med.;* 8/7/80; pp. 322-324.
Mirowski et al., "Clinical Treatment of Life-Threatening Ventricular Tachyarrhythmias with the Automatic Implantable Defibrillator," *Amer. Heart Journal;* 8/81, pp. 265-270.
Schuder et al., "Waveform Dependency in Defibrillating 100 kg Calves," *Devices & Tech. Meeting*, NIH, 1982; p. 174.
J. L. Jones & R. E. Jones, "Defibrillator Waveshape Optimization," *Devices & Tech. Meeting*, NIH, 1982; p. 175.
J. L. Jones & R. E. Jones, "Improved Defibrillator Waveform Safety Factor with Biphasic Waveforms," *The American Journal of Physiology*, 7/83; 245:1; pp. H60-H65.
Schuder et al., "Ultrahigh-Energy Hydrogen Thyratron/SCR Bidirectional Waveform Defibrillator," *Medical & Biological Engineering & Computing*, Jul. 1982, pp. 419-424.
R. A. Winkle, "The Implantable Defibrillator in Ventricular Arrhythmias," *Hospital Practice*, Mar. 1983, pp. 149-165.

(List continued on next page.)

*Primary Examiner*—Francis Jaworski
*Attorney, Agent, or Firm*—Gottlieb, Rackman & Reisman

[57] ABSTRACT

A method and apparatus for applying an asymmetric biphasic exponential waveform countershock to the heart useful in an implantable cardioverter or defibrillator, wherein the second phase has a start amplitude of substantially one half that of the first phase, and wherein the polarity of a capacitor discharging through a current path including the heart is reversed. A voltage reversing circuit may include a voltage shifter which shifts voltage associated with switching elements in the circuit to reduce voltage stresses in the switching elements.

18 Claims, 4 Drawing Sheets

OTHER PUBLICATIONS

Schuder et al., "Transthoracic Ventricular Defibrillation in the 100 kg Calf with Symmetrical One-Cycle Bidirectional Rectangular Wave Stimuli," *IEEE Transactions on Biomedical Engineering*, vol. BME-30, No. 7; Jul. 1983; pp. 415-422.

Schuder et al., "Defibrillation of 100 kg Calves with Asymmetrical, Bidirectional, Rectangular Pulses," *Cardiovascular Research;* 1984:18; pp. 419-426.

Schuder et al., "One-Cycle Bidirectional Rectangular Wave Shocks for Open Chest Defibrillation in the Calf," *Abs. Amer. Soc. Artificial Internal Organs;* 9:16.

Schuder et al., "Development of Automatic Implanted Defibrillator," *Devices & Tech. Meeting,* NIH; p. 206 (1981).

Tang et al., "Ventricular Defibrillation Using Biphasic Waveforms of Different Phasic Duration," *PACE:* vol. 10; Mar.-Apr. 1987.

Tang et al., "Strength Duration Curve for Ventricular Defibrillation Using Biphasic Waveforms," *The North Amer. Society of Pacing and Electrophysiology;* May 2, 1987; p. 49.

Winkle et al., "Improved Low Energy Defibrillation Efficacy in Man Using a Biphasic Truncated Exponential Waveform," *JACC;* vol. 9, No. 2; Feb. 1987; p. 142A.

B. D. Lindsay et al., "Prospective Evaluation of a Sequential Pacing and High-Energy Bidirectional Shock Algorithm for Transvenous Cardioversion in Patients with Ventricular Tachycardia," *Therapy and Prevention,* vol. 76, No. 3 (Sep., 1987).

S. Saksena et al., "A Prospective Evaluation of Single and Dual Current Pathways for Transvenous Cardioversion in Rapid Ventricular Tachycardia," PACE, vol. 10, pp. 1130-1141 (Sep.-Oct., 1987).

S. Saksena et al., "Developments for Future Implantable Cardioverters and Defibrillators," PACE, vol. 10, pp. 1342-1358 (Nov.-Dec., 1987).

METHOD AND APPARATUS FOR APPLYING ASYMMETRIC BIPHASIC TRUNCATED EXPONENTIAL COUNTERSHOCKS

This application is a continuation of Ser. No. 397,637 filed Aug. 23, 1989 and now abandoned, which is a continuation of Ser. No. 145,515 filed Jan. 19, 1988 and now abandoned.

TECHNICAL FIELD

This invention relates to apparatus for applying countershocks to the heart. More particularly it relates to cardioverters and defibrillators which supply truncated exponential pulses, and to implantable devices of this type.

BACKGROUND ART

Ventricular arrhythmias are potentially lethal. In the instance of chaotic, non-coordinated muscle contraction, known as fibrillation, death can ensue within minutes after onset. To convert the fibrillation to an organized, slower cardiac rate, an electrical countershock is given. A high energy pulse of 400 joules or less is applied across the chest wall using an external defibrillator. However, such external defibrillators are located in hospitals and in rescue vehicles. Because death can ensue within ten minutes, medical assistance may arrive too late to resuscitate the patient.

For patients who have survived an episode of ventricular fibrillation, there is a high probability of reoccurrence. In addition, patients who have experienced sustained symptomatic ventricular tachycardia are at risk in that such arrhythmias may convert to fibrillation. It is these patients who benefit from an implantable cardioverter or defibrillator.

An implantable cardioverter or defibrillator must be capable of sensing ventricular cardiac electrical activity, of determining if the sensed electrical activity is ventricular tachycardia or fibrillation and of enabling a circuit which then delivers a high energy pulse to electrodes associated with the heart to perform cardioversion (a shock in synchronization with the cardiac cycle) or defibrillation.

In prior implantable defibrillators, a truncated exponential pulse (trapezoidal pulse) of 25 joules or more has been utilized. Such a trapezoidal pulse is produced by a few external defibrillators but, more commonly, a damped sine wave is used. External defibrillators require a higher energy source, of up to 400 joules, because of energy dissipation through the chest wall.

Schuder et al. in "Ultrahigh-Energy Hydrogen Thyratron/SCR Bidirectional Waveform Defibrillator," *Med & Biol. Eng. & Comput.* Vol. 20, pp. 419–424 (July, 1982), show a symmetrical bi-directional truncated exponential waveform having less than 10% droop, so as to approximate a rectangular waveform, and a schematic diagram of an apparatus for generating such a waveform. The bi-directional pulse as described by Schuder et al. is incorporated into a rather large external defibrillator. Such bi-directional pulses can defibrillate and do not appear to influence adversely the outcome of subsequent attempts to defibrillate. However, much of the energy stored in the capacitor is lost, because the charge on the capacitor at the end of each phase must be dumped when the voltage is still a large fraction of the initial charge voltage.

In an implantable defibrillator, it is necessary to conserve space so that the implantable unit is not large. Further, because battery energy is finite in an implantable unit, any increase in efficiency that can be attained by fuller utilization of the stored energy (as measured in joules) or reduction in defibrillation threshold is of critical importance. Such increase in efficiency extends the useful life of the implant, thus reducing the frequency of implant replacement and the cost associated with an inefficient device due to the cost of the device itself, and surgical and hospital expenses incurred as a result of replacement. While replacement is a rather simple procedure, the patient is nevertheless exposed to the risks inherent in any form of surgery. In addition, reduction in defibrillation threshold, while saving energy, also has the beneficial effect of reducing the discomfort experienced by the patient when the defibrillation shock is applied.

DISCLOSURE OF THE INVENTION

It is an object of the invention to provide a method and apparatus for applying electrotherapy to the heart which is energy efficient.

It is another object of the invention to provide a method and apparatus for defibrillating the heart at a relatively low defibrillation threshold.

It is an additional object of the invention to provide an apparatus for applying electrotherapy to the heart which may be implanted within the body.

It is a further object of the invention to provide a method and apparatus for applying biphasic countershocks to the heart by using a single capacitor or a single capacitor bank for energy storage.

It is still another object of the invention to provide a switching circuit which permits the use of a single capacitor bank in an apparatus and method for applying electrotherapy to the heart, which circuit minimizes voltage stresses on the components therein.

In accordance with the method of the invention, electrotherapy is applied to the heart by way of conductive leads electrically connected to electrodes associated with the heart. The leads and electrodes conduct pulses of electric current to the heart. These pulses include a first truncated exponential waveform of a first polarity having a first start amplitude and a first end amplitude; and a second truncated exponential waveform of a second polarity opposite that of said first polarity. The second truncated exponential waveform has a second start amplitude and a second end amplitude. The second start amplitude is lower than the first start amplitude. The second start amplitude may be substantially equal to the first end amplitude. Preferably the second start amplitude is equal to substantially one-half of the first start amplitude or is equal to between forty and sixty percent of the first start amplitude. The first truncated exponential waveform and the second truncated exponential waveform are applied by charging a capacitor to a voltage corresponding to the first start amplitude, discharging the capacitor through the leads to a voltage corresponding to the first end amplitude, reversing polarity of connection to the leads and discharging the capacitor to a voltage corresponding to the second end amplitude. The capacitor may be disconnected from the leads for a predetermined period of time before reversing the polarity of connection of the capacitor to the leads.

Also in accordance with the invention, an apparatus for administering electrotherapy to the heart comprises a recognition means responsive to an electrical signal from the heart for determining when the heart is in need of electrotherapy, a capacitive energy storage means for storing electrical energy to be applied to the heart, an energy source means for providing electrical energy to the energy storage means, a conductor means for conducting the stored electrical energy from the energy storage means to the heart, and a connection means for connecting the conductor means with a first polarity to administer a first shock, and with a second polarity opposite said first polarity to administer a second shock after administering of the first shock.

The connection means comprises a first switch means for connecting a first terminal of the energy storage means to a first lead to the heart, a second switch means for connecting a second terminal of the energy storage means to a second lead to the heart, a third switch means for connecting the first terminal of the energy storage means to the second lead to the heart, a fourth switch means for connecting the second terminal of the energy storage means to the first lead to the heart, and timing means for closing the first switch means and the second switch means at a first time, for opening the first switch means and the second switch means at a second time after the first time, for closing the third switch means and the fourth switch means at a third time after the second time, and for opening the third switch means and the fourth switch means at a fourth time after the third time.

Preferably the first switch means includes two switches connected in series. Further, the apparatus preferably includes a voltage reducing means for reducing the voltage across the fourth switch means at a fifth time, the fifth time being after the second time and before the third time. The voltage reducing means shifts the voltage from across the fourth switch means so that it is across the first switch means. When the first switch means includes two switches connected in series, the apparatus may further comprise a first resistor connected across a first of the two switches, a fifth switch means having a first terminal connected to the second terminal of the energy storage means and a second resistor connecting a second terminal of the fifth switch means and a connection point between the first of the two switches and a second of the two switches. The apparatus further comprises a capacitor connected between the connection point and the second terminal of the energy storage means.

BRIEF DESCRIPTION OF THE DRAWINGS

Further objects, features and advantages of our invention will become apparent upon consideration of the following detailed description in connection with the drawings, in which:

FIG. 6A to FIG. 6I represent waveforms associated with the circuit of FIG. 5.

BEST MODE FOR CARRYING OUT THE INVENTION

The invention is described herein with respect to an implantable defibrillator which is believed to be its primary, most important and most urgent area of application. However, it will be recognized in the art that the invention may be applied to external defibrillators and to cardioverters as well.

Figure 1:
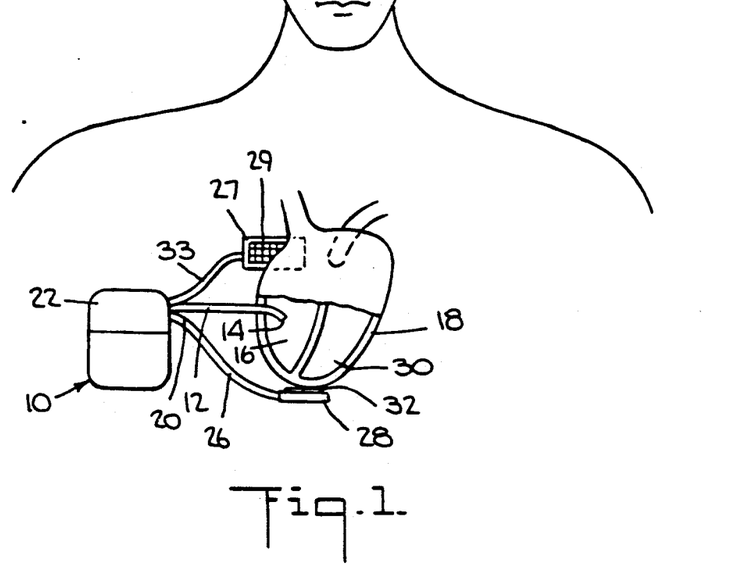
FIG. 1 is a simplified, schematic view along a section through a thorax showing an implantable defibrillator in accordance with invention and its connection to leads associated with the heart.

Referring to FIG. 1, an implantable defibrillator 10 is implanted subcutaneously in a patient, generally in an abdominal muscle. An epicardial sensing lead 12 including an insulated conductor wire is in electrical continuity with a ventricular sensing electrode 14 used for sensing ventricular electrical activity. Alternatively a pervenous sensing lead may be threaded through an appropriate vein and positioned in the right ventricle 16 of the heart 18. A terminal assembly (not shown) at the proximal end 20 of sensing lead 12 is inserted into a first receptacle (not shown) within the neck 22 of implantable defibrillator 10. The terminal assembly of sensing lead 12, when inserted in its respective receptacle, is electrically connected to the insulated conductor and to the circuitry of the defibrillator 10. This capsulated in case 24 is a low impedance battery, using lithium vanadium pentoxide or lithium silver vanadium pentoxide chemistry.

A terminal assembly (not shown) of a second lead 26 is connected to implantable defibrillator 10 via a second receptacle in neck 22 of defibrillator 10. The insulated conductor wire of lead 26 is tunneled subcutaneously. An electrode pad 28 at the distal end of lead 26 is sutured onto the epicardial surface of the left ventricle 30 of the heart 18 during a thoracotomy or median sternotomy A subxiphoid approach may also be used. A defibrillatory electrode 32, which acts as a cathode for the delivery of the first phase of biphasic defibrillation shocks, protrudes slightly from the cardiac surface of electrode pad 28 of lead 26.

A base patch 27 having an electrode 29 which is preferably epicardial, but as noted below may be subcutaneous, located at the distal end of a third lead 33, has a proximal terminal received in a third receptacle (not shown) in neck 22 of defibrillator 10. Electrode 29 acts as an anode for the delivery of the first phase of biphasic defibrillation shocks.

While lead 26 with its electrode 32 and lead 33 with its electrode 29 are epicardial, either lead may be epicardial or pervenous. Of importance, it is also contemplated that for defibrillation one lead and electrode may be pervenous, while the other may be a subcutaneous patch. The increased efficiency of defibrillation of an asymmetric biphasic truncated exponential pulse in accordance with the invention would thus permit the installation of an implantable defibrillator without necessitating opening the chest cavity. This greatly increases the desirability of the apparatus according to the invention by reducing the risk of patient morbidity or mortality as a result of risks associated with a more extensive surgical procedure.

Figure 2:
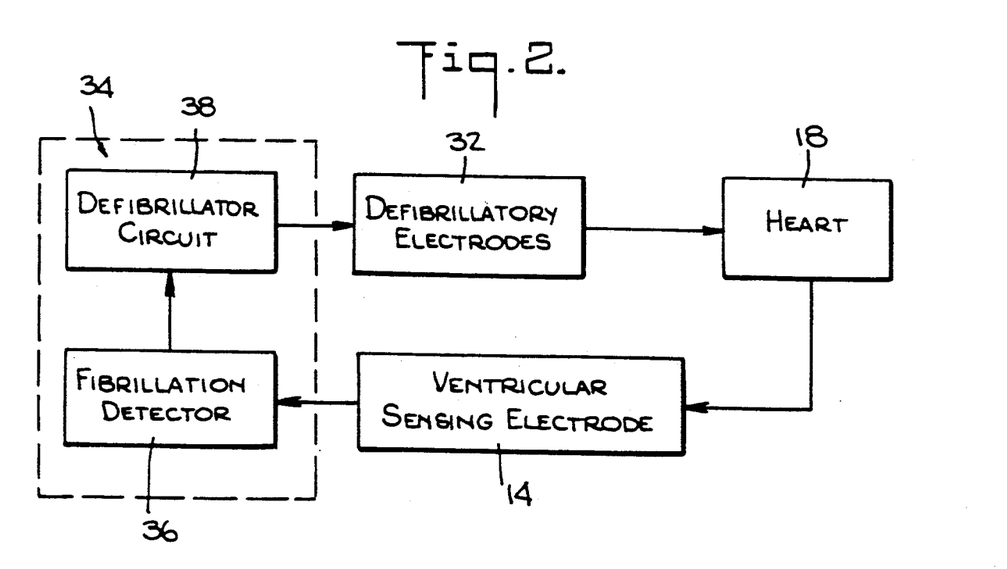
FIG. 2 is a conceptual block diagram of the implantable defibrillator of FIG. 1.

Referring to FIG. 2, the circuitry 34 within the titanium case 24 is comprised of a fibrillation detector 36 (or a tachycardia detector for purposes of cardioversion) which may include any of several well-known arrhythmia detectors and a countershock or defibrillation circuit 38. Electrical activity generated by the ventricles 16,30 of the heart 18 is transmitted by the ventricular sensing electrode 14 to the fibrillation detector 36. If the detected ventricular activity is classified as fibrillation, as indicated by a chaotic, non-rhythmic electrical activity, defibrillator circuit 38 is enabled.

Figure 3:
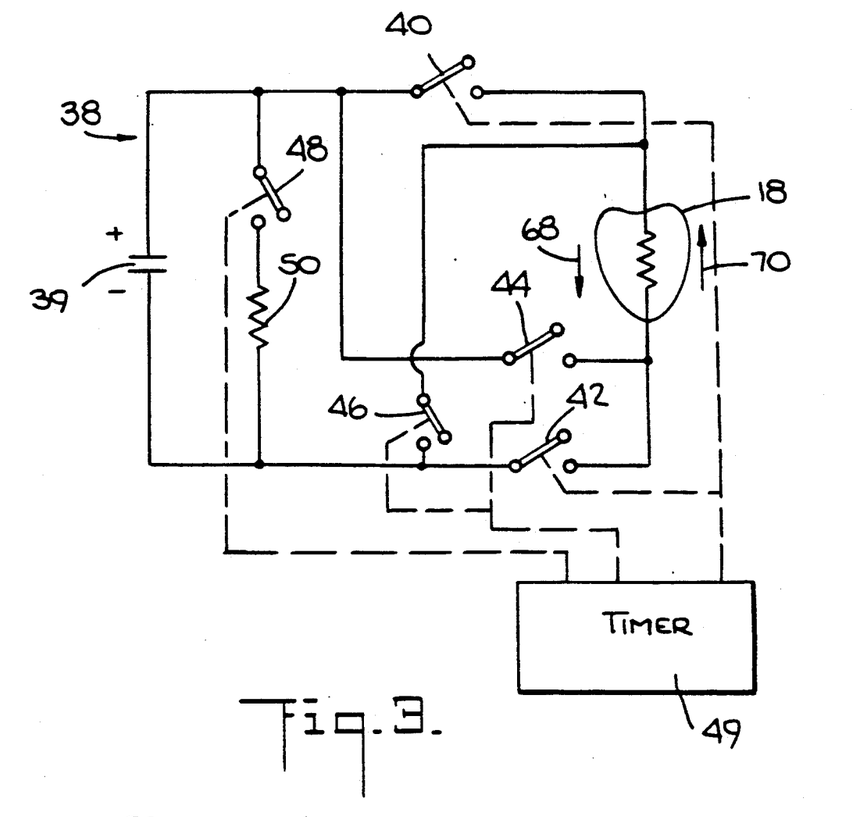
FIG. 3 is a conceptual schematic diagram of a circuit for use in the apparatus according to the invention.

Referring to FIG. 3, the pulse forming or defibrillator circuit 38 is, in, simplified or conceptual form, comprised of a capacitor 39, a series of switches 40, 42, 44, and 46, which appropriately open and close in response to signals from a timer circuit 49 (as described below, also with reference to FIG. 4), to deliver defibrillation shocks to the heart 18, and optionally, a switch 48 and a resistive load 50.

Figure 4:
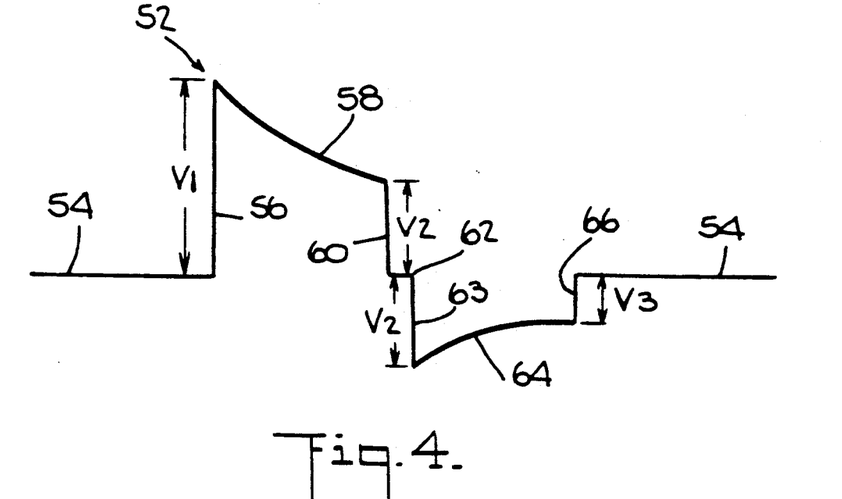
FIG. 4 illustrates the waveform of the defibrillatory pulse of an implantable defibrillator in accordance with the invention.

Referring to FIG. 4, an asymmetric biphasic exponential waveform 52, as recorded between defibrillatory electrodes 29 and 32 is measured from a baseline 54. Waveform 52 has a leading edge 56 of amplitude V1. The leading edge is followed by an exponential decay 58 of 2 to 8 milliseconds (for a time which may preferably be equal to approximately 0.7 times the time constant of capacitor 39 and the defibrillation resistance of the heart) to a second voltage level V2, at trailing edge 60, which waveform 52 returns to baseline 54. A zero voltage period 62 of 0.1 to 5.0 milliseconds is followed by a polarity reversal. The voltage V2 is then applied to the heart at leading edge 63 and a second exponential decay 64 occurs, which is preferably of the same duration, as the first decay 58. The voltage falls to a third voltage level V3 at trailing edge 66, from which it returns to baseline 54.

Asymmetric biphasic exponential waveform 52 is generated by utilizing circuit 38 in the following manner: capacitor 39 is charged by an energy source (not shown in FIG. 3) to a voltage V1 of the polarity shown. Switches 40 and 42 are closed by timer circuit 49 placing capacitor 39 in series with the heart 18. Current flows through the heart 18 in the direction of the arrow 68 discharging the capacitor to voltage V2. Switches 44, 46 and 48 are open during this time. Then, capacitor 39 is disconnected from the heart 18 and the voltage level of capacitor 39 is held at V2 when timer circuit 49 causes switches 40 and 42 to open. After a short no current interval, current is then caused to flow through the heart 18 in the direction as shown by the arrow 70 when timer circuit 49 causes switch 44 and switch 46 to close, thereby discharging capacitor 39 to voltage V3. The second phase is truncated when timer circuit 49 causes switch 44 and switch 46 to open (all others having remained open). Optional switch 48 may then be closed causing capacitor 39 to discharge into resistive load 50.

Thus, the defibrillatory pulse is actually made up of two pulses of current which travel through the heart first in one direction and then in the opposite direction increasing the probability of depolarizing and then rendering refractory a larger volume of the cardiac muscle fiber. The refractoriness makes it unlikely for fibrillation to continue. However, if fibrillation does continue, the capacitor is recharged and an additional pulse or pulses having the waveform illustrated in FIG. 4 may be administered.

Figure 5:
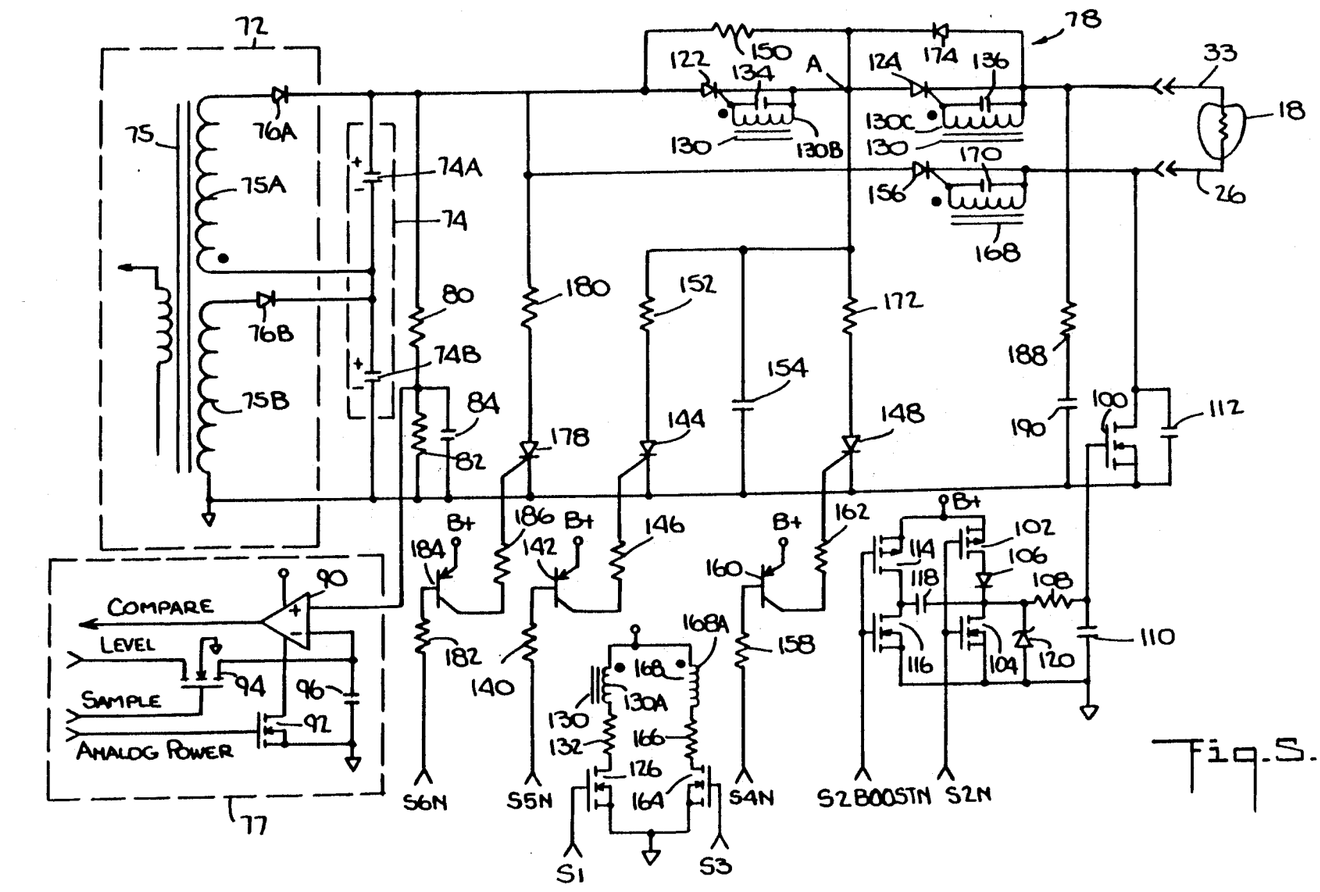
FIG. 5 is a detailed schematic diagram of a circuit for use in the preferred embodiment of the apparatus according to the invention.

Referring to FIG. 5, the conceptual circuit of FIG. 3 is implemented. FIG. 5 includes a charging circuit 72 of conventional type for charging a single capacitor bank 74, a comparator circuit 77 for providing electrical signals indicative of the voltage to which capacitor bank 74 has been charged and a switching circuit shown generally at 78, which is a practical implementation of the concept of FIG. 3. While timer circuit 49 is not described, the necessary waveforms and their relationships in time are described below with respect to FIG. 6B to FIG. 6G.

When fibrillation is detected by fibrillation detector 36 (FIG. 2) capacitor bank 74 is charged by capacitor charging circuit 72. Charging circuit 72 may be any of several well-known circuits which have provisions for a "soft start" so that the large current demands placed on the battery at the beginning of the charge cycle are somewhat reduced in magnitude and provisions for low battery voltage detection means for temporarily halting the charge cycle to permit battery recovery should the battery voltage drop to a predetermined low level.

While capacitor bank 74 would preferably include only a single capacitor, the limitations in capacitor technology, and in particular the limitations of aluminum electrolytic capacitors are such that the maximum working voltage is not sufficient to withstand the maximum voltage to which the capacitor must be charged. Thus, capacitor bank 74 may be made up of two capacitors 74A and 74B which are connected in series and charged by charging circuit 72. Specifically, capacitor 74A is charged by a secondary winding 75A of a step up transformer 75 through a diode 76A. In a similar manner, capacitor 74B is charged by current from secondary winding 75B of transformer 75 through diode 76B.

A voltage divider including resistors 80 and 82 and a smoothing capacitor 84 provide an output voltage to comparator circuit 77 which is proportional to, but a small fraction of, the voltage across capacitor bank 74.

Comparator circuit 77 includes an integrated circuit comparator 90. The positive supply voltage from the battery, appropriately increased in level by, for example, voltage doubling is always supplied to circuit 90. However, the negative supply voltage to comparator 90 is connected through a MOSFET 92 which becomes conductive only upon application of an analog power enable signal to the gate thereof. Comparator 90 is thus turned off most of the time for purposes for saving power and turned on only during time periods when a voltage "measurement" must be made.

A sample-and-hold circuit including a MOSFET 94 and a capacitor 96 provides a reference voltage to one input of comparator 90. The other input of comparator 90 is connected to the junction between resistors 80 and 82. When the charging cycle is initiated, power is applied to comparator 90 through MOSFET 92 and a voltage level applied to the drain of MOSFET 94 is stored on capacitor 96 by supplying a sample pulse to the gate of MOSFET 94. It is desirable to use a sample-and-hold circuit, with the storage capacitor thereof located in close physical proximity to the comparator chip, and when in the hold mode, electrically isolated from the remainder of the circuitry of defibrillator 10, so that the large currents in the circuitry do not induce spurious voltages on the capacitor and detract from the accuracy of comparator circuit 77.

When capacitor bank 74 has charged to the appropriate voltage level, and the output of comparator 90 switches states, charging is complete. Charging circuit 72 is then turned off. A voltage representative of V2 is then loaded on to capacitor 96 of comparator circuit 77. A shock is initiated by operation of time circuit 49 immediately for defibrillation or in synchronism with detected heart activity if cardioversion is being performed. However, it is desirable to reconfirm the presence of a tachyarrhythmia before timer circuit 49 operates to supply a shock.

During sensing and pacing, defibrillation lead 26 acts as a return for electrical conduction to the heart. The pacing and/or sensing signals from this lead are conducted through MOSFET 100 for this purpose. Thus, MOSFET 100 must be at least partially switched on at all times except during the charging of capacitor bank 74 at which time MOSFET 100 is switched off to provide protection against accidental discharge. MOSFET 100 is turned on by a switching circuit including MOSFETS 102 and 104. When the signal S2N (FIG. 6B) is at ground potential MOSFET 104 is off and MOSFET 102 is turned on. Diode 106 becomes conductive thus raising the potential of the gate of MOSFET 100 by conducting current through resistor 108. Capacitor 110 smoothes the voltage at the gate of MOSFET 100 and prevents transient impulses from turning on MOSFET 100. Capacitor 112 protects MOSFET 100 against currents due to electrosurgery by providing a bypass between the source and drain thereof.

Figure 6A:
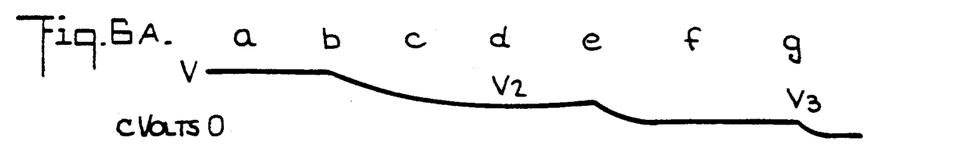
Figure 6B:
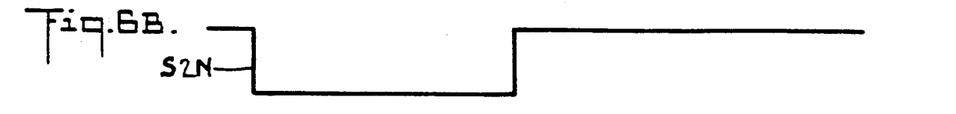
Figure 6C:
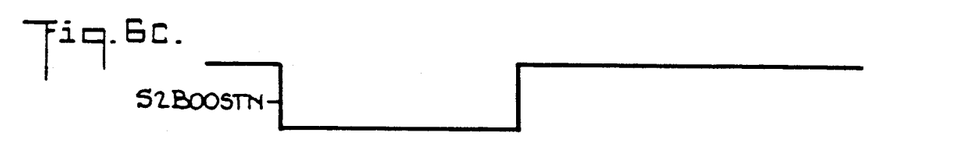

While MOSFET 100 is held on so that its internal resistance is in the order of 20 to 30 ohms for sensing and pacing (when S2N is at logic zero), in order to conduct a defibrillation pulse MOSFET 100 must be put into a very low resistance condition or "turned on hard" so that its internal impedance is of a mere fraction of an ohm. This is accomplished through the action of MOSFETS 114 and 116 as well as capacitor 118. When S2BOOSTN from timer circuit 49 is at a logic high voltage level, MOSFET 114 is turned off and MOSFET 116 is turned on. Capacitor 118 is charged through diode 106 so that the side facing diode 106 is at a voltage close to that of the positive supply voltage (the doubled battery voltage). As shown in FIG. 6C, for the application of a defibrillation pulse, S2BOOSTN is dropped to ground potential by timer circuit 49. This turns off MOSFET 116 and turns on MOSFET 114. The result is to place capacitor 118 in series with the positive supply voltage so that approximately twice that voltage is applied across the source and drain of MOSFET 104 (off at that time). This results in MOSFET 100 being turned on hard. Zener diode 120 serves to limit the voltage applied between the source and gate of MOSFET 100 so that it is not damaged. FIG. 6A illustrates that after capacitor bank 74 has been charged to voltage V1, S2N goes low and then S2BOOSTN goes low shortly thereafter (FIG. 6B and FIG. 6C). MOSFETS 102, 104, 114 and 118 may all be on a single type CD4007 chip.

In order to provide a defibrillation shock to the heart, it also necessary to turn on SCR 122 and SCR 124. This is accomplished when timer circuit 49 provides a pulse S1 (not shown in FIG. 6A to FIG. 6H) to the gate of MOSFET 126 completing a circuit through the primary winding 130A of transformer 130, current limiting resistor 132 and MOSFET 126. The surge of current through primary winding 130A induces a voltage in a first secondary winding 130B and a second secondary winding 130C of transformer 130. If the polarities of connection of the windings of transformer 130 are as indicated in FIG. 5, SCR 122 and SCR 124 are triggered. False triggering is prevented by capacitor 134 across secondary 130B and capacitor 136 across secondary 130C.

Figure 6D:
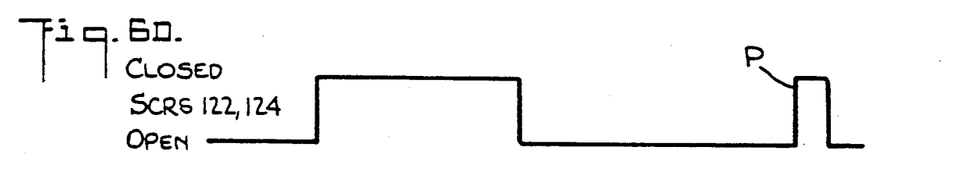

When MOSFET 100 and SCRs 122 and 124 have been turned on (the state of the latter two devices being represented by FIG. 6D) current is conducted through SCR 122, SCR 124, to a lead terminal in neck 22 of defibrillator 10, along defibrillation lead 33, through the heart 18, along defibrillation lead 26, to another lead terminal in neck 22 of defibrillator 10, and finally through MOSFET 100, all connected in series across capacitor bank 74.

After the output of comparator 90 has changed states due to the voltage across capacitor bank 74 being reduced to voltage V2, which may be some fixed fraction of the voltage V1, timer circuit 49 causes S2N and S2BOOSTN to return to a logic high state thus turning off MOSFET 100, commutating SCR 122 and SCR 124 (FIG. 6D) and terminating the initial phase of discharge of capacitor bank 74. At this point capacitor bank 74 is electrically disconnected from the heart.

Figure 6E:
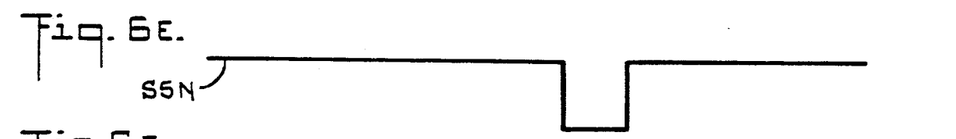
Figure 6F:
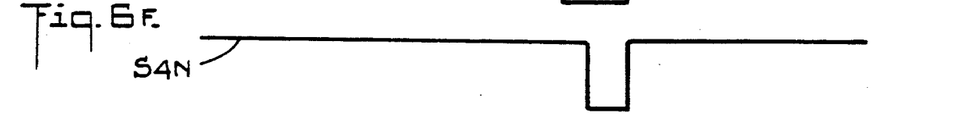

For a period of time following the first phase, timer circuit 49 does not interact with the circuit of FIG. 5. In other words, there is a delay of 0.1 millisecond to 5 milliseconds during which no current is delivered to the heart 18. After this delay, capacitor bank 74 is reconnected to the heart with its polarity reversed. First, timer circuit 49 causes the voltage S5N (FIG. 6E) applied to resistor 140 to go from a positive logic level to zero volts (ground). Since the emitter of transistor 142 is connected to the positive supply voltage, this causes transistor 142 to turn on which in turn causes triggering of SCR 144 by way of current conducted through resistor 146. Before this occurs, the full voltage of capacitor bank 74 appears across SCR 148. However, when SCR 144 is turned on much of this voltage is slowly shifted to appear across SCR 122 due to the voltage division action of resistor 150 and resistor 152. Typically, resistor 150 will have a resistance value at least 10 times as great as that of resistor 152. The voltage is gradually shifted due to the discharge time of a capacitor 154 through the series combination of resistor 152 and SCR 144. A practical time constant may be on the order of 10 to 50 microseconds. This shift in voltage is represented by the change in the voltage at point A (the connection point of SCR 122 and SCR 124) as shown in FIG. 6H. The slight jog in voltage at point X of FIG. 6H after the shift, occurs when SCR 148 is turned on as described below.

Timer circuit 49 causes the heart 18 to be connected to capacitor bank 74 by turning on SCR 148 and SCR 156. SCR 148 is triggered by changing the voltage S4N (FIG. 6F) applied to resistor 158 from a logic high state to a logic zero state (ground), thus turning on transistor 160 (the emitter of which is connected to the positive supply voltage) and triggering SCR 148 due to current conducted through resistor 162.

Figure 6G:
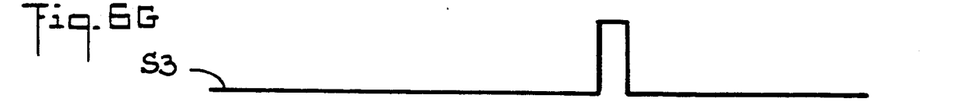
Figure 6H:
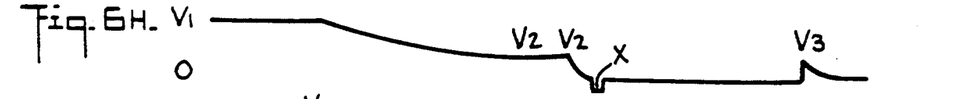
Figure 6I:
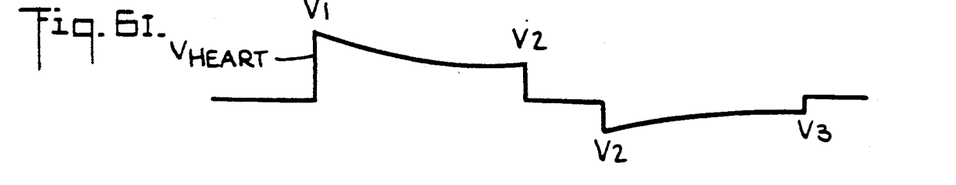

To turn on SCR 156 the voltage S3 at the gate at MOSFET 164 is changed from ground to a positive logic voltage (FIG. 6G). Current begins to flow through the series circuit including the primary winding 168A of a transformer 168, current limiting resistor 166 and MOSFET 164. The changing current in primary winding 168A induce a voltage in secondary winding 168B of transformer 168 thus triggering SCR 156. The capacitor 170 prevents false triggering of SCR 156 in a manner similar to that of capacitors 134 and 136.

The path of current from capacitor bank 74, at this time includes SCR 156, a lead connection terminal within neck 22 of defibrillator 10, defibrillation lead 26, the heart 18, defibrillation lead 33, a second lead terminal within neck 22 of defibrillator 10, a diode 174, a resistor 172 (which has a value of no greater than several ohms) and finally SCR 148. Initially, voltage V2 (FIG. 4 and FIG. 6A) is applied to the heart and decays to voltage V3 due to discharge of capacitor bank 74. This second phase of the shock applied to the heart is truncated at a time so that its duration is preferably equal to the duration of the first phase (of opposite polarity) applied to the heart. Alternatively a third voltage representative of a desired value of V3 may be loaded on to capacitor 96 of comparator circuit 77, and a change in output of comparator 90 used to initiate truncation. To accomplish truncation, timer circuit 49 again supplies a short pulse to the gate of MOSFET 126, again triggering SCR 122 (as represented by pulse P, FIG. 6D). Capacitor bank 74 is thus discharged through SCR 122, resistor 172 and SCR 148.

It will be recognized that the start voltage of the second phase of the defibrillation shock will be slightly lower than that at the end of the first phase due to a small voltage drop across resistor 172. It is believed that voltages for V2 from sixty percent to forty percent of V1 produce the lowest defibrillation threshold. This voltage drop across resistor 172 is therefore inconsequential. It will be recognized that some resistance, rather than a simple short, is required to reduce current so as to protect SCR 122 and SCR 148 when capacitor bank 74 is being discharged.

An additional SCR 178, and a resistor 180 having a resistance of, for example, 50 ohms (which is comparable to the defibrillation path resistance of the heart) form a test load for the battery, capacitor charging circuit 72 and capacitor bank 74 and provide a means for dissipating the energy of capacitor bank 74 if charging is performed but no shock is applied to the heart. At appropriate times, as is well-known in the art, a voltage S6N applied to a resistor 182 is changed from a positive logic voltage to ground thus turning on a transistor 184 having an emitter connected to the positive supply voltage and triggering SCR 178 when current is conducted through a resistor 186.

In summary, with reference to sequential points and intervals in time in FIG. 6A to FIG. 6H, as shown thereon:

Charging of capacitor bank 74 to voltage V1 occurs until point a.

Capacitor bank 74 is placed in series with the heart by turning on MOSFET 100 and then closing SCR 122 and SCR 124 simultaneously at point b.

Capacitor bank 74 is allowed to discharge to voltage V2 during interval c.

Capacitor bank 74 is disconnected from the heart by opening MOSFET 100, SCR 122 and SCR 124 at point d.

After a short delay, capacitor bank 74 is reconnected to the heart with inverted polarity by first closing SCR 144 to slowly shift voltage from SCR 148 to SCR 122 and then by closing SCR 148 and SCR 156 (the latter at point e).

Voltage V2 is applied to the heart and capacitor bank 74 is discharged to voltage V3 during interval f.

The second phase is truncated at V3 by closing SCR 122 which shunts charge in capacitor bank 74 away from the heart through the path defined by SCR 122, resistor 172 and SCR 148 during time interval g.

A major advantage of the circuit of FIG. 5 is that no SCR's are exposed to rapid positive voltage changes at any time. Resistor 150, resistor 152, capacitor 154 and SCR 144 preload SCR 122 into its blocking mode prior to application of voltage V2 to the heart. The elimination of rapid positive voltage changes makes possible the use of commonly available and inexpensive switching components. For example, the SCRs which conduct defibrillation current may all be of type 2N6509, while MOSFET 102 may be a type IRF450. Building a more dependable and less complex energy delivery system by using such proven components is of major importance because in an implantable defibrillator any departure from high reliability would be anathema.

There are additional advantages to the circuit of FIG. 5. The circuit can be used to provide single monophasic pulses or sequential monophasic pulses by modifying the timing of appropriate control signals from timer circuit 49.

For additional protection against currents induced by electrosurgery a bypass circuit including resistor 188 and capacitor 190 may be provided.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

We claim:

1. A method for applying electrotherapy to the heart by way of conductive leads electrically connected to electrodes associated with the heart, said leads and electrodes being for conducting pulses of electrical current to the heart, comprising the steps of:
   charging a capacitor to a voltage corresponding to a first start amplitude;
   discharging said capacitor through said leads to a voltage corresponding to a first end amplitude; to thereby apply a first truncated exponential waveform of a first polarity to said leads, said first truncated exponential waveform having said first start amplitude and said first end amplitude;
   reversing polarity of connection of said capacitor to said leads; and
   discharging said capacitor to a voltage corresponding to a second end amplitude to thereby apply a second truncated exponential waveform of a second polarity opposite that of said first polarity to said leads; said second truncated exponential waveform having second start amplitude and said second end amplitude;
   said second start amplitude being lower than said first start amplitude.

2. The method of claim 1, wherein said second start amplitude is substantially equal to said first end amplitude.

3. The method of claim 2, wherein said second start amplitude is equal to substantially one-half of said first start amplitude.

4. The method of claim 2, wherein said second start amplitude is equal to between a forty and sixty percent of said first start amplitude.

5. The method of claim 1, wherein said second end amplitude is equal to substantially one-half of said second start amplitude.

6. The method of claim 1, further comprising the step of disconnecting said capacitor from said leads for a predetermined period of time before reversing the polarity of connection of said capacitor to said leads.

7. The method of claim 6, wherein said predetermined time is between 0.1 milliseconds and 5.0 msec.

8. The method of claim 1, further comprising the step of delaying application of said second truncated exponential waveform for a predetermined period of time after application of said first truncated exponential waveform.

9. The method of claim 8, wherein said predetermined time is between 0.1 and 5.0 milliseconds.

10. An apparatus for administering electrotherapy to a heart comprising:

a recognition means responsive to an electrical signal from the heart for determining when the heart is in need of electrotherapy;

a capacitive energy storage means for storing electrical energy to be applied to the heart;

an energy source means for providing said electrical energy to said energy storage means;

conductor means for conducting said stored electrical energy from said energy storage means to the heart; and connection means for connecting said conductor means with a first plurality to administer a first shock, and with a second polarity opposite said first polarity to administer a second shock, after administration of said first shock; said connection means including:

a first switch means for connecting a first terminal of said energy storage means to a first lead to the heart;

a second switch means for connecting a second terminal of said energy storage means to a second lead to the heart;

a third switch means for connecting said first terminal of said energy storage means to said second lead to the heart;

a fourth switch means for connecting said second terminal of said energy storage means to said first lead to the heart; and timing means for closing said first switch means and said second switch means at a first time, for opening said first switch means and said second switch means at a second time after said first time, for closing said third switch means and said fourth switch means at a third time after said second time, and for opening said third switch means and said fourth switch means at a fourth time after said third time.

11. The apparatus of claim 10, wherein said capacitive energy storage means is a single capacitor.

12. The apparatus of claim 10, wherein said capacitive energy storage means includes two capacitors connected in series, each of said two capacitors being of equal capacitance.

13. The apparatus of claim 10, wherein said first switch means includes two switches connected in series.

14. The apparatus of claim 10, further comprising voltage reducing means for reducing the voltage across said fourth switch means at a fifth time, said fifth time being after said second time and before said third time.

15. The apparatus of claim 14, wherein said voltage reducing means shifts said voltage from across said fourth switch means to across said first switch means.

16. The apparatus of claim 10, wherein said first switch means includes two switches connected in series, further comprising a first resistor connected across a first of said two switches, a fifth switch means having a first terminal connected to the second terminal of said energy storage means, a second resistor connecting a second terminal of said fifth switch means and a connection point between said first of said two switches and a second of said two switches; and a capacitor connected between said connection point and said second terminal of said energy storage means.

17. The apparatus of claim 10, further comprising energy dissipating means for dissipating energy stored in said energy storage means.

18. The apparatus of claim 17, wherein said energy dissipating means includes an energy dissipating resistor and switch means for connecting said resistor to said energy storage means to discharge said energy storage means.

* * * * *

UNITED STATES PATENT AND TRADEMARK OFFICE
CERTIFICATE OF CORRECTION

PATENT NO. : 5,083,562

DATED : January 28, 1962

INVENTOR(S) : P. E. de Coriolis et al.

It is certified that error appears in the above-identified patent and that said Letters Patent is hereby corrected as shown below:

In FIG. 1, the lead line from numeral 20 should extend to the left (proximal) end portion of sensing lead 12, rather than to the left end portion of lead 26.

In FIG. 1, the lower portion of implantable defibrillator 10 (i.e., the portion below neck 22) should be identified by the numeral 24.

In FIG. 2, the broken line rectangle enclosing defibrillator circuit 38 and fibrillation detector 36 should be identified by the numeral 24.

In column 4, line 26, "capsulated in" should read -- circuitry is encapsulated in a titanium case 24. Also encapsulated in --.

In column 5, line 16, a comma (,) should be inserted after the numeral "32".

In column 6, line 65, "time" should read -- timer --.

In column 10, line 2, after "available" and before "and", the word -- rugged -- should be inserted.

In column 10, line 46, after "having" and before "second", the word -- a -- should be inserted.

9. In column 10, line 58, the word "a" should be deleted.

UNITED STATES PATENT AND TRADEMARK OFFICE
CERTIFICATE OF CORRECTION

PATENT NO. : 5,083,562
DATED : January 28, 1992
INVENTOR(S) : P. E. de Coriolis et al It is certified that error appears in the above-indentified patent and that said Letters Patent is hereby corrected as shown below:

In column 11, line 21, "plurality" should read -- polarity --.

Signed and Sealed this

Sixteenth Day of November, 1993

*Attest:*

BRUCE LEHMAN

*Attesting Officer*     Commissioner of Patents and Trademarks